US011058158B2

(12) United States Patent
Vanneste et al.

(10) Patent No.: US 11,058,158 B2
(45) Date of Patent: Jul. 13, 2021

(54) HEAD PROTECTION HOOD WITH INTEGRATED FRAME

(71) Applicant: BeMicron, Charleroi (BE)

(72) Inventors: Vincent Vanneste, Thimougies (BE); Siegfried De Smet, Maarkedal (BE)

(73) Assignee: BeMicron, Charleroi (BE)

( * ) Notice: Subject to any disclaimer, the term of this patent is extended or adjusted under 35 U.S.C. 154(b) by 147 days.

(21) Appl. No.: 16/347,443

(22) PCT Filed: Oct. 24, 2017

(86) PCT No.: PCT/EP2017/077201
§ 371 (c)(1),
(2) Date: May 3, 2019

(87) PCT Pub. No.: WO2018/082975
PCT Pub. Date: May 11, 2018

(65) Prior Publication Data
US 2019/0274381 A1 Sep. 12, 2019

(30) Foreign Application Priority Data

Nov. 4, 2016 (BE) .................................. 2016/5820
Nov. 4, 2016 (EP) .................................. 16197317
(Continued)

(51) Int. Cl.
*A41D 13/11* (2006.01)
*A41D 13/02* (2006.01)
(Continued)

(52) U.S. Cl.
CPC ...... *A41D 13/1153* (2013.01); *A41D 13/1184* (2013.01); *A41D 13/02* (2013.01);
(Continued)

(58) Field of Classification Search
CPC ............ A41D 13/1153; A41D 13/1184; A41D 13/02; A41D 13/1218; A42B 1/046;
(Continued)

(56) References Cited

U.S. PATENT DOCUMENTS 5,575,277 A * 11/1996 Lutz ....................... A62B 18/08
128/201.11
5,653,225 A * 8/1997 Schegerin .............. A62B 17/04
128/201.22
(Continued)

FOREIGN PATENT DOCUMENTS

| CN | 104225835 A | 12/2014 |
| FR | 2 928 260 A1 | 9/2009 |

(Continued)

OTHER PUBLICATIONS

International Search Report dated Nov. 29, 2017, issued in corresponding International Application No. PCT/EP2017/077201, filed Oct. 24, 2017, 4 pages.

*Primary Examiner* — Amy Vanatta
(74) *Attorney, Agent, or Firm* — Christensen O'Connor Johnson Kindness PLLC (57) ABSTRACT

A head protection hood having an outer surface configured to contact a surrounding environment, an inner surface configured to contact the head of a user, a head passage section, a face opening delimited by an edge at the eyes of the user, and a breathing area is provided. The head protection hood includes a frame connected along the edge of the face opening, that receives a visor and that has a first lip resting against the head of the user at an area situated between the root and the tip of the nose, at the front region, at the temples, and at the infra-orbital regions of the face of the user, thus forming a visual compartment separated from said breathing area. The frame further comprises a second (Continued)

peripheral lip situated between the first lip and the visor, the second peripheral lip extending from the frame towards said surrounding environment.

13 Claims, 8 Drawing Sheets (30) Foreign Application Priority Data

Apr. 13, 2017 (BE) .................................. 2017/5262
Apr. 13, 2017 (EP) .................................. 17166558

(51) Int. Cl.
*A42B 1/046* (2021.01)
*A42B 1/048* (2021.01)
*A42B 1/247* (2021.01)
*A61F 9/02* (2006.01)
*A62B 17/04* (2006.01)

(52) U.S. Cl.
CPC ............... *A42B 1/046* (2013.01); *A42B 1/048* (2013.01); *A42B 1/247* (2013.01); *A61F 9/029* (2013.01); *A62B 17/04* (2013.01)

(58) Field of Classification Search
CPC ....... A42B 1/048; A42B 1/247; A42B 1/0181; A42B 1/041; A62B 17/04; A62B 18/084; A62B 18/082; A62B 9/04; A62B 18/08; A62B 17/00; A61F 9/029; A61F 9/06
USPC .......................................................... 2/901
See application file for complete search history.

(56) References Cited

U.S. PATENT DOCUMENTS

| 6,604,248 | B1* | 8/2003 | Brown | A41D 13/02 |
| | | | | 2/456 |
| 7,062,786 | B2* | 6/2006 | Stinton | A41D 13/0005 |
| | | | | 2/2.15 |
| 8,955,516 | B2 | 2/2015 | Gaffney et al. | |
| 2005/0115567 | A1* | 6/2005 | Bridges | A62B 18/04 |
| | | | | 128/206.21 |
| 2010/0258131 | A1* | 10/2010 | Gaffney | A62B 18/08 |
| | | | | 128/206.24 |
| 2013/0180523 | A1* | 7/2013 | Huggins | A41D 13/11 |
| | | | | 128/202.22 |
| 2014/0190476 | A1* | 7/2014 | Stinton | A62B 17/04 |
| | | | | 128/201.23 |

FOREIGN PATENT DOCUMENTS

FR 3 016 271 A1 7/2015
WO 2016/083496 A1 6/2016

\* cited by examiner

HEAD PROTECTION HOOD WITH INTEGRATED FRAME

FIELD OF DISCLOSURE

Embodiments of the present disclosure relate to a head protection hood having:
- an outer surface intended to be in contact with a surrounding environment,
- an inner surface intended to be in contact with the head of a user,
- a head passage section,
- a face opening delimited by an edge at the eyes of the user, and
- a breathing area, the hood comprising a frame which is connected along the edge of the face opening, which receives a visor and which has a first lip resting on the head of the user at an area situated between the bridge and tip of the nose, at the front region, at the temples and at the infra-orbital regions of the face of the user, thus forming a visual compartment separated from the breathing area.

BACKGROUND

A head protection hood is known from document FR3016271 which discloses a hood having an outer surface intended to be in contact with a surrounding environment, an inner surface intended to be in contact with the head of a user, a head passage section and a face opening delimited by an edge at the eyes of the user. According to this prior art document, the hood is further provided with protective eyewear in a frame setting ensuring space between a visor and the support on the face of the user, the protective eyewear being fixed to the hood at the face opening so that the eyewear and the hood form a single article. More specifically, the setting is fixed to the edge of the face opening of the hood by the edge (lip) of the setting which rests on and is supported by the face of the user. For example, as shown in this prior art document, the edge (the lip) intended to abut the face of the user is stitched onto the periphery of the face opening (opening of the hood) so the hood and the protective eyewear form a single article. Furthermore, a section of the hood forms a breathing mask which can also be stitched/fixed onto the lower section of the eyewear at the support edge (lip). Note that, according to this prior art document, the visor is not intended to be removable, as a specific procedure for washing the hood/the overalls comprising a hood is proposed to protect the visor during a step of washing the garment.

This type of head protection hood is particularly used in aseptic or sterile environments where the user must be isolated from the surrounding environment. This is particularly shown in environments such as clean rooms and laboratories where vaccines and medicines are prepared. On the one hand, in this type of environment, the user needs to be as isolated as possible so they do not contaminate the environment in which they are working and, on the other hand, it is sometimes a question of isolating the user themselves from dangerous and/or harmful substances.

When an operator is brought to work in a sterile environment, they must particularly ensure that they do not contaminate the equipment they wear. In this way, the operator must respect the strict dressing procedures, which are only meaningful if the protective equipment that they are using is entirely sterile itself. To that end, the overalls and hoods are generally provided after sterilization, in sealed packages whose easy openings allow the sterile equipment to be grasped. In addition, more specifically in relation to the hoods provided with a visor, it is necessary that the latter be not only sterile but also perfectly clean to ensure an accurate view and working comfort for the user.

Unfortunately, even if a hood according to document FR 3016271 has certain advantages including a reduction of the presence and formation of steam, it appears that it is not optimal and is prone to rapid wear. In fact, a first problem found with a hood according to this prior art document resides in the fact that the edge (lip) resting on the face of the user generally comprises stitches fixing the protective eyewear to the hood. These stiches are in direct contact with the skin of the face of the user, which is particularly irritating and may cause itching. Furthermore, the presence of stitches on the support edge encourages air to enter the visual compartment, as each stitch means that the support edge is perforated, which is contrary to the elimination of the problems of steam formation.

A second problem, this time irrespective of the means fixing the frame setting to the hood (stitching, gluing, etc.), is that in practice, during the procedures of cleaning the hood to which the protective eyewear is fixed, the support edge (lip) is quickly damaged, and more and more over the course of the wash cycles. In fact, during machine cleaning and/or during drying, the hood is subjected to different mechanical pressures, notably during spin cycles wherein it is pressed against the walls of the drum of the machine. Inevitably, in such a case, the fabric of the hood fixed over the support edge (lip) exerts traction thereupon, causing damage but also progressive separation of the eyewear from the hood. In the event wherein the eyewear-hood connection is implemented by stitching, the perforations resulting from the stitching grow bit by bit as a result of the mechanical pressures until the support edge (lip) ends up being torn by the stitching thread. As a result, the support edge can no longer definitely ensure the seal of the visual compartment with respect to the breathing compartment and/or as the fabric of the hood detaches from the protective eyewear. This is evidently problematical, as indicated above, as the aim is to isolate the operator from the environment and vice versa.

A third problem then is that the manufacturing of the hood where the eyewear is connected by stitching, or any other means, over the support edge (lip) is difficult to implement on a large scale: in fact, it is particularly complicated to automate the manufacturing of such hoods where precise stitching must be carried out on a support edge (lip) which, due to its nature, must be narrow in width. In fact, this support edge (lip) is intended to closely fit to the facial features and must not be irritating for the user, this implying that the width of the support edge (lip) be reduced while ensuring an appropriate seal between the visual compartment and the breathing compartment.

SUMMARY

The object of the disclosure is to overcome the disadvantages of the prior art by providing a head protection hood for which the cleaning and sterilization steps are simple, this in parallel with:
significant or complete elimination of problems of condensation and steam forming on the visor;
optimal user comfort, mainly at the support edge (lip) in contact with the skin of the face of the user;

lack of deterioration (distortion) of the hood over time during wash/dry cycles, specifically a lack of disconnection of the hood and the protective eyewear and a lack of damage to the support edge (lip); and ease of manufacturing the head protection hood, this manufacturing being capable of being automated and not requiring considerable work or at least a significant workforce.

To solve this problem, a head protection hood is provided according to the disclosure wherein, as indicated above, the frame further comprises a second peripheral lip situated between the first lip and the visor, the second peripheral lip extending from the frame in the direction of the surrounding environment.

According to the disclosure, any appropriate means may be used in order to connect the frame along the face opening. For example, the hood-protective eyewear (hood-frame) connection may be implemented by stitching, by gluing or by any other means allowing a link to be ensured between the two elements. According to a first example, the second peripheral lip of the frame may be stitched to the hood along the edge of the face opening. The frame may also, according to a second example, be definitively connected (fixed) to the hood by clamping the fabric forming the hood between two sections of the second peripheral lip, this along the face opening. In the latter case, the second peripheral lip may be, according to the disclosure, formed of two lip sections which are able to fit together (for example, through a male-female system), the fabric of the hood and, specifically, the periphery of the face opening of the hood then being clamped between these two lip sections of the second peripheral lip.

Such a hood according to the disclosure, if the frame is provided with a second peripheral lip situated between the first lip and the visor, the second peripheral lip extending from the frame towards the surrounding environment, is not only comfortable but also durable and easy to manufacture, particularly by automating certain manufacturing steps.

In fact, the presence of the second peripheral lip according to the disclosure allows, when the hood-protective eyewear (hood-frame) connection is implemented by stitching, the stitches pressing against the skin of the user to be avoided. Furthermore, the presence of the second peripheral lip according to the disclosure allows problems of distortion/damage to the support edge (lip) to be eliminated and easily facilitates the same implementation of the hood according to the disclosure. More specifically, the fabric of the hood is connected (for example, stitched or glued) to the second peripheral lip according to the disclosure and not to the first lip resting against the head of the user: the second lip being specifically adapted for stitching and/or gluing work during the preparation or manufacturing, no stitch touches the user in the face area where the first lip rests when the hood-protective eyewear connection is implemented by stitching; no mechanical pressure is exerted by the fabric forming the hood on the first lip of the frame during wash/dry cycles or during wearing if the first lip is not connected to the fabric; and the second peripheral lip forms an outer border of the frame wherein an automated fixing, for example by stitching or by gluing, may be implemented, this second peripheral lip not having to be narrow in width as is the case for the first support lip.

Furthermore, such a hood according to the disclosure is particularly advantageous as it has not only a visor which can be easily placed onto and removed (removable visor) from the frame, but it also has a visual compartment which is separated, preferably in a sealed manner, from a breathing area. This separation of the breathing area and the visual compartment is ensured through the first lip of the frame which is in contact with and rests on the face of the user at an area situated between the bridge and tip of the nose, preferably at the arch of the nose, at the front region, at the temples and at the infra-orbital regions of the face of the user, thus forming a visual compartment separated from the breathing area. Preferably, this contact and this resting of the first lip of the frame are implemented along the entire periphery of the visual compartment in order to truly isolate, preferably to isolate in a sealed manner, the visual compartment from a breathing area. Furthermore, the hood according to the disclosure ensures optimal vision while eliminating the presence of blind spots and ensuring peripheral vision on every side of the visor, particularly the lower part thereof.

The term "breathing area" means, in the scope of the present disclosure, an area which includes the nostrils and mouth of the operator, this area capable, for example, of being formed of fabric or, to the contrary, free of fabric. In the first case, the nostrils and the mouth of the operator are included in the hood. In the second case, the nostrils and the mouth of the operator may be protected by a mask separate from the hood, for example, by a disposable mask which does not, however, prevent the problem of steam and condensation in the visor.

The term "visual compartment" thus means, in the scope of the present disclosure, a compartment delimited by the upper, lower and lateral walls of the frame but also by a visor closing the frame in front of the eyes of the user, and by an area for the face of the user delimited by the first lip of the frame resting against an area situated between the bridge and the tip of the nose, preferably at the arch of the nose, at the front region, at the temples and at the infra-orbital regions. Preferably, according to the disclosure, the visual compartment thus delimited is provided so that users wearing corrective glasses may use the hood without being irritated by a visor which presses against the rim of the glasses.

With a hood according to the disclosure, the problem of steam and condensation forming is also significantly reduced or totally eliminated as the visual compartment, formed by the frame pressed onto the face of the operator by the first lip and by the visor closing the frame, is completely isolated, preferably isolated in a sealed manner, from the breathing area and thus from air breathed out by the operator.

A hood according to the disclosure further allows the steps of cleaning and sterilization of the protective equipment to be greatly simplified. In fact, the ability to remove the visor (removable visor) easily and quickly from the frame of the hood ultimately allows, on the one hand, an element formed by the hood provided with its frame to be available and, on the other hand, an element made of plastic (or any other appropriate material) consisting of the visor to be available. The visor may be intended for one use and may be disposed of and replaced after each use. Furthermore, it is possible to direct the hood and its frame, without its visor, towards a classic cleaning and/or sterilizing (decontaminating) treatment facility while the visor may be dispatched, with a view to its reuse, towards an appropriate cleaning system which will not damage it. This is important as the visors are generally formed of a transparent plastic material which cannot be subjected to classic sterilization and even less a series of sterilizations such as those to which the hood must be nevertheless subjected: the visor could lose its transparency, for example, due to the heat or due to the specific rays used during sterilization. The rays cause, as an example, rapid yellowing of a plastic visor after only a few sterilization cycles. Naturally, an alternative is to simply replace the used visor with a new clean visor on the hoods once decontaminated.

Advantageously, according to the disclosure, the frame has a first frame section extending from an outer surface of the second peripheral lip towards the surrounding environment and a second frame section extending towards the head of the user from an inner surface of the second peripheral lip, the second frame section being provided with the first lip.

Preferably, according to the disclosure, the first frame section has air flow holes. Such air flow holes, preferably present at the upper and/or lower walls of the frame and recessed with respect to the visor, further allowing, but without being essential, the problem of steam and condensation forming in the visor to be eliminated. In fact, it is possible that the user may sweat slightly inside the visual compartment, which could also lead to the presence of steam and condensation in the visor. However, due to the air flow holes present on the frame according to the disclosure, a flow of air is ensured in the visual compartment in a way that further avoids any steam and condensation forming. This air flow is natural, as the hot air which is contained in the visual compartment has a tendency to exit via the holes present in the upper wall of the frame, this leading to a natural aspiration of fresh air from the surrounding environment (from the clean room) and via the holes present in the lower wall of the frame, the result being that the temperatures of the air in the visual compartment and in the surrounding environment are practically identical, which minimizes or eliminates the presence of steam and condensation.

Advantageously, according to the disclosure, the first lip is a continuous and/or flexible lip. The fact that the first lip of the frame is continuous and/or flexible allows a better seal or complete seal of the visual compartment all around its periphery to be ensured, which allows its isolation to be further enforced with respect to the breathing area.

Preferably, according to the disclosure, the frame forms an integral part of the hood. As indicated above, the frame may be definitively connected along the edge of the face opening of the hood, this being, for example, by means of stitching or gluing or by any other appropriate means. Note that, according to the disclosure, only the visor may be removed before subjecting the hood to the cleaning and sterilization steps not compatible with the visor. It is thus not appropriate to replace a frame on a sterilized hood each time but simply to removably fix a visor to the frame, which is quick and allows a posteriori handling to be reduced, for example, during the dressing procedures.

Preferably, according to the disclosure, the frame is formed of a material resistant to the means of sterilization such as gamma or Beta rays, autoclaving or ethylene oxide treatments. For example, the frame according to the disclosure may be formed of silicon or thermoplastic polyurethane (TPU), even if any other type of appropriate material falls under the scope of the present disclosure.

Advantageously, the frame according to the disclosure is formed of a rubber material containing at least one nitrile group.

Advantageously, the head protection hood according to the disclosure comprises an auto-adjustment system for the frame to the face of the operator, the auto-adjustment system being placed at the back of or on at least one of the sides of the hood. Such an auto-adjustment system for the frame allows the frame to be positioned so it perfectly connects to the face of the operator, typically at an area situated between the bridge and tip of the nose (preferably at the arch of the nose), at the front region, at the temples and at the infra-orbital regions. To that end, at least one strap connected to the fabric on the side of the hood or connected to the frame itself is present so the operator can correctly position the frame with respect to their visual area. Furthermore, the presence of such an auto-adjustment system allows a uniformly distributed tightening pressure to be exerted, which ensures comfort for the user but also a seal or at least a practically complete seal of the visual compartment.

Preferably, according to the disclosure, the visor comprises a system for fixing to the frame. According to the disclosure, the visor may be placed and removed through either the inside or outside of the hood, or equally through the inside or outside. In order for the visor to be correctly kept on the frame according to the disclosure, it may be slid into a groove present on the frame or slotted together using a male-female system, the male and female parts finding one another either on the frame or on the visor. In the latter case, the visor may, for example, be provided with pins gliding into the notches present on the periphery of the frame.

Preferably, according to the disclosure, the visor is made of a transparent plastic material or any other appropriate material, for example, polycarbonate. This material may be, for example, rigid or flexible, tinted or not, scratch resistant or not, acid resistant or not, according to the fields of application. It is understood that the visor according to the disclosure may have other properties.

Advantageously, according to the disclosure, the frame is provided with an active breathing system, i.e. a system which removes external air in order to inject/introduce it into the breathing area (breathing compartment).

Preferably, the head protection hood according to the disclosure forms an integral part of a protective garment for clean room and similar. In fact, the hood according to the disclosure can just as well be an individual section or form an integral part of a protective garment, for example, as integral protective overalls. It is understood that the hood may be connected by any means of fixing to the protective garment, for example, by stitching or fixing by means of a zip, snap fasteners or by means of any other appropriate fixing.

Advantageously, the head protection hood according to the disclosure forms an integral part of a protective garment such as overalls, such as those described in document EP2303044 comprising an outer surface intended to be in contact with a surrounding environment and an inner surface intended to be in contact with a user, a first and second leg section connected together by an opening in the crotch area, a first and second sleeve and torso section to which the first and second sleeves are connected by a connected end and the first and second leg sections also by a connected end, the torso section comprising a head passage section, the overalls further comprising at least one grip area in contact with the inner surface in the torso section.

Preferably, the head protection hood according to the disclosure forms an integral part of a protective garment such as overalls whose opening is situated in the torso section, for example, at the spine.

Other embodiments of a head protection hood according to the disclosure are indicated in the attached claims.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

In the figures, identical or similar elements bear the same references.

Figure 1A:
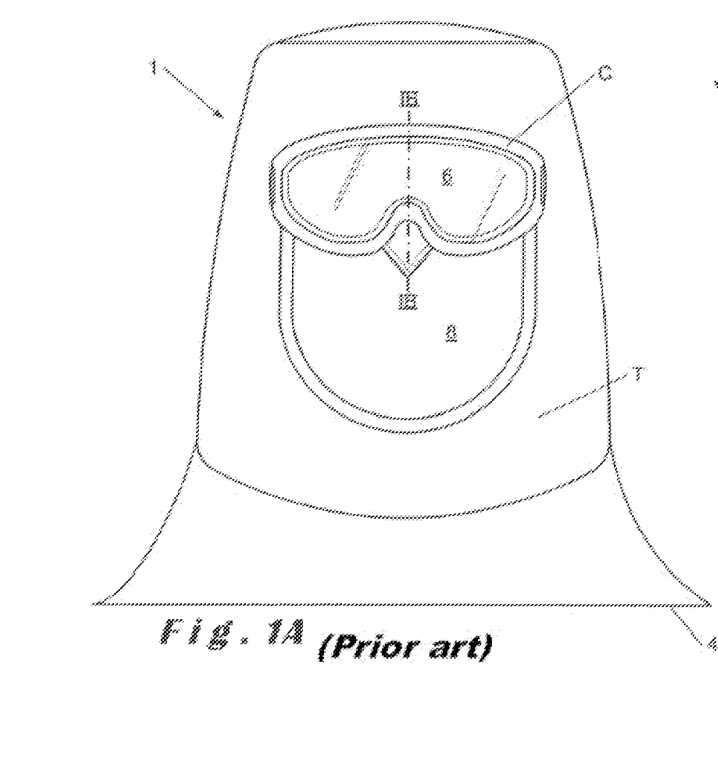
FIG. 1A is a front view of a head protection hood according to the prior art.

FIG. 1A shows a hood 1 according to the prior art which has an outer surface 2 intended to be in contact with the surrounding environment, an inner surface 3 intended to be in contact with the head of a user, a head passage section 4 and a face opening 5 at the eyes of the user. The face opening 5 is delimited by an edge along which a frame C is connected, arranged to receive a visor 6. The frame has a lip L1 (not visible in FIG. 1A but visible in FIG. 1B) resting on the head of the user at an area situated between the bridge and tip of the nose, at the front region, at the temples and at the infra-orbital regions of the face of the user, thus forming a visual compartment 7 separated from a breathing area 8. This resting of the lip L1 of the frame C allows a visual compartment 7 to be delimited and isolated from a breathing area 8.

Figure 1B:
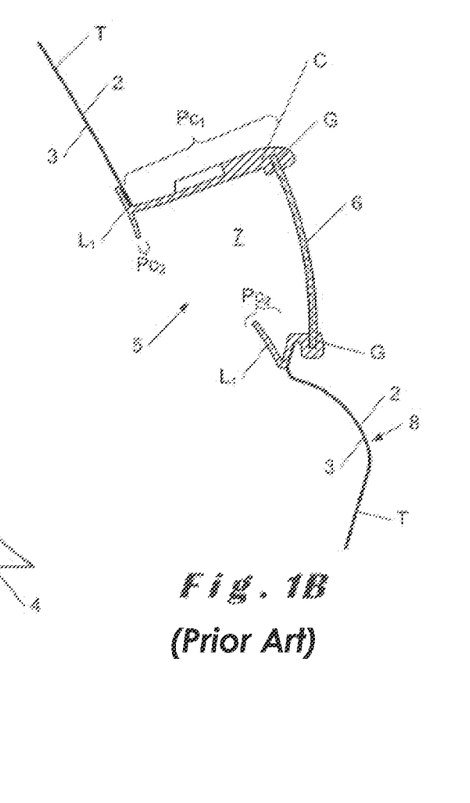
FIG. 1B is a sectional view according to Axis II of a head protection hood according to the prior art.

As show in FIG. 1B, the frame C is connected to the fabric T forming the hood 1 along the edge of the face opening 5 and has a groove G into which a visor 6 is inserted. The frame C further comprises a lip L1 to which the fabric T of the hood 1 is connected, this lip L1 being continuous and being intended, when the hood 1 is worn by a user, to be in contact with and to rest against the face of the user at an area situated between the bridge and the tip of the nose, at the front region, at the temples and at the infra-orbital regions, thus forming a visual compartment 7 separated from a breathing area 8. More specifically, the frame C has a first frame section Pc1 extending towards the surrounding environment from the outer surface 2 of the hood 1 and a second frame section Pc2 extending towards the head of the user from the inner surface 3 of the hood 1, the second frame section Pc2 being provided with the lip L1.

As shown, with this head protection hood 1 according to the prior art, the inner surface 3 of the hood 1 is connected along the lip L1. Thus, when the hood 1-frame C connection is implemented by stitching, the stitches (not shown) are in direct contact with the skin of the user and cause itching. Furthermore, the stitches dictate that the lip L1 is perforated, which forms entry points for air and does not allow a proper seal of the visual compartment 7 to be ensured. In addition, that the hood 1-frame C connection is implemented by stitching, by gluing or by any other method onto the lip L1 implies that the latter is subjected to mechanical pressures, the fabric T pulls on the lip L1, for example, during wash/dry cycles or even during the dressing procedure. The result is that the lip L1 is distorted (damaged) over time and the head protection hood 1 according to the prior art is not durable. It is also noted that it is not easy to connect the hood 1 to the lip L1 because the lip L1 resting against the head of the user must be relatively thin and narrow or else it will be irritating for the user.

Figure 2A:
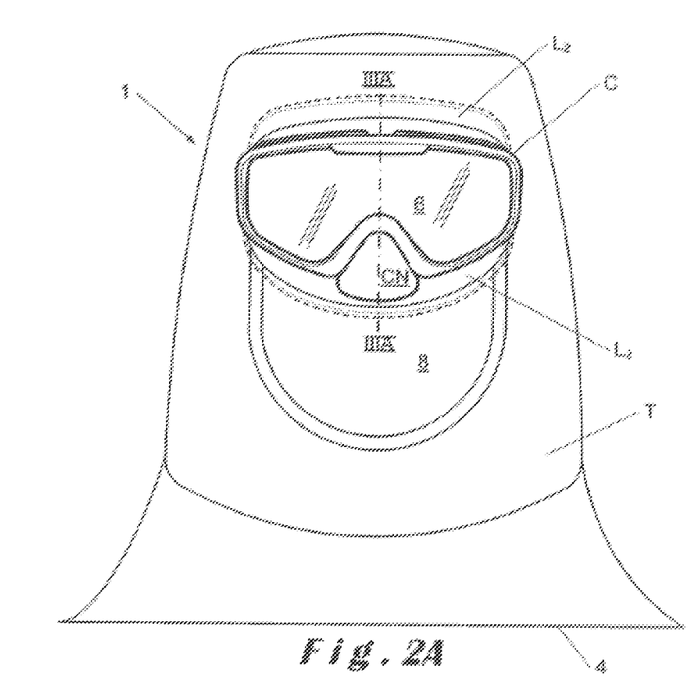
FIGS. 2A, 2B and 2C are front views of different embodiments of head protection hoods according to the disclosure.
Figure 2B:
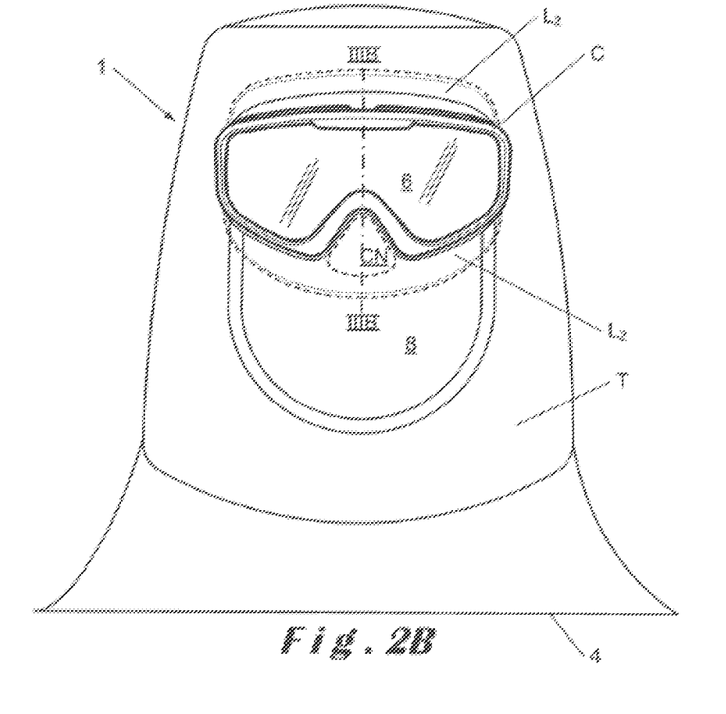
Figure 2C:
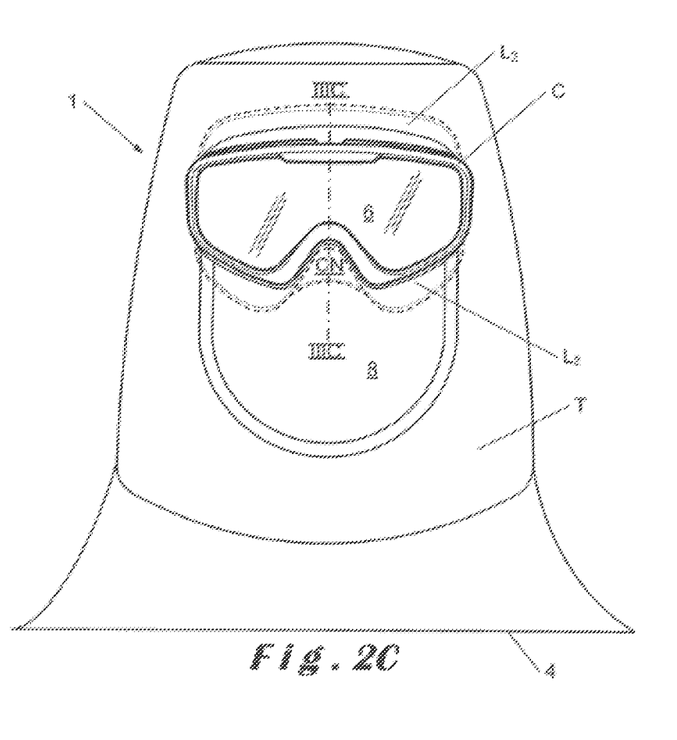

FIGS. 2A, 2B and 2C show three embodiments of a head protection hood according to the disclosure. In the first embodiment according to FIG. 2A, the head protection hood 1 comprises a frame C provided with a first lip L1 (not visible) and a second peripheral lip L2 situated between the first lip L1 and the visor 6, the second peripheral visor L2 extending towards the surrounding environment. On this second peripheral lip L2, the fabric T forming the hood 1 is fixed, for example, by stitching or by gluing. Naturally, the fabric T forming the hood 1 may be fixed to the outer surface L2ex or to the inner surface L2int of the peripheral lip L2. As shown, according to this first embodiment, the frame C comprises a muffler CN which forms an integral part of the protective eyewear (that is, of the frame C). The nose of the operator is then confined in the muffler CN which is made from a material which is either identical or not to that of the frame C.

FIG. 2B incorporates the same features as mentioned in FIG. 2A, with the difference that the muffler CN according to this second embodiment is formed of fabric T, which is connected to the peripheral lip L2, for example, by stitching or by gluing.

According to a third embodiment shown in FIG. 2C, which incorporates the same features as the two preceding figures, the hood 1 is provided with a partial muffler CN which partially covers the nose.

Figures 3A, 3B:
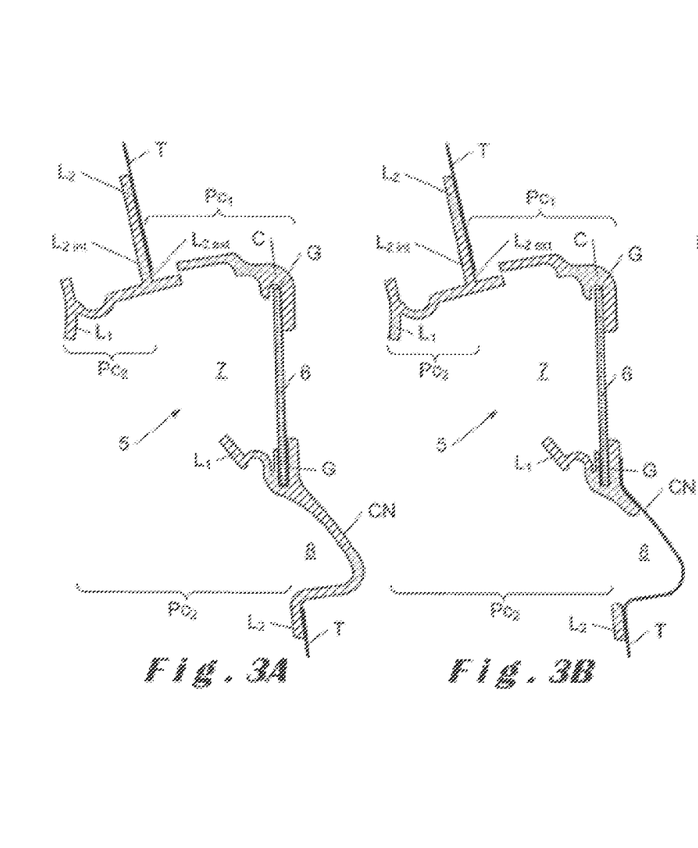
FIGS. 3A, 3B and 3C are sectional views according to Axes IIIA, IIIB and IIIC respectively of embodiments of FIGS. 2A, 2B and 2C.
Figure 3C:
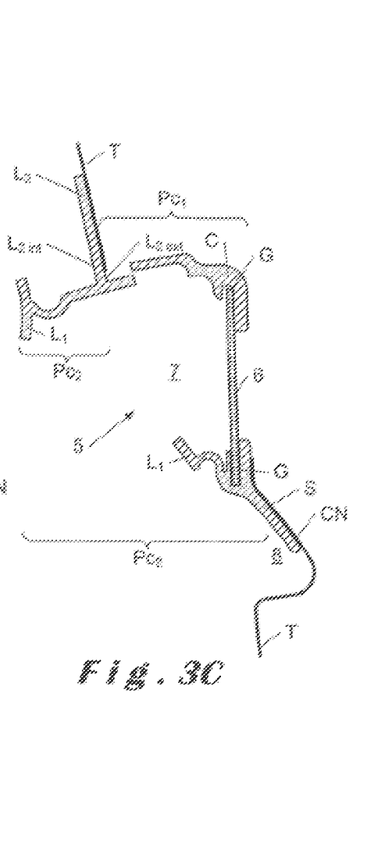

FIGS. 3A, 3B and 3C are sectional views of FIGS. 2A, 2B and 2C according to Axes IIIA, IIIB and IIIC respectively. As shown in FIG. 3A, the frame C is connected to the fabric T forming the hood 1 along the edge of the face opening 5 and has a groove G into which a visor 6 is inserted. Naturally, any other means of fixing the visor 6 to the frame C form an integral part of the present disclosure such as, for example, using clips (interlocking) or other. The frame C comprises a first lip L1 which is continuous and intended, when the hood 1 is worn by a user, to be in contact with and to rest against the face of the user at an area between the bridge and tip of the nose, at the front region, at the temples and at the infra-orbital regions, thus forming a visual compartment 7 separated from a breathing area 8. The frame C also comprises a second peripheral lip L2 having an outer surface L2ext and an inner surface L2int, the fabric T of the hood 1 being, according to this embodiment, fixed/connected (for example, by stitching or by gluing) to the outer surface L2ext of the second peripheral lip L2. It is understood that the fabric T of the hood 1 may be, according to an alternative according to the disclosure, fixed/connected (for example, by stitching or by gluing) to the inner surface L2int of the second peripheral lip L2. More particularly, the frame C has a first frame section Pc1 extending towards the surrounding environment from the outer surface L2ext of the second peripheral lip L2 and a second frame section Pc2 extending towards the head of the user from the inner surface L2int of the second peripheral lip L2, the second frame section Pc2 being provided with the first lip L1. According to this first embodiment, the breathing area 8 is partially formed by a muffler CN section of the frame C connected to the second peripheral lip L2, this muffler CN covering the nose of the user.

FIG. 3B shows a second embodiment according to the disclosure and incorporates the same elements as shown in FIG. 3A, with the difference that the muffler CN according to this second embodiment is formed of material, which is connected on the one hand to the peripheral lip L2 and on the other hand to a hood section close to the visor 6, for example, by stitching or by gluing. According to an alternative to the embodiment shown in FIG. 3B according to the disclosure, a muffler CN may not be present (no material in front of the nose of the user) and the user then places a mask (for example, a disposable mask) over their nose.

FIG. 3C shows a third embodiment according to the disclosure and incorporates the same elements as shown in FIGS. 3A and 3B, with the difference that the muffler CN according to this third embodiment is formed of fabric T, which is connected on the one hand to the peripheral lip L2 and on the other hand to a frame section close to the visor 6 and in the form of a projection S allowing the fabric T forming the muffler CN to be "guided".

Figure 4:
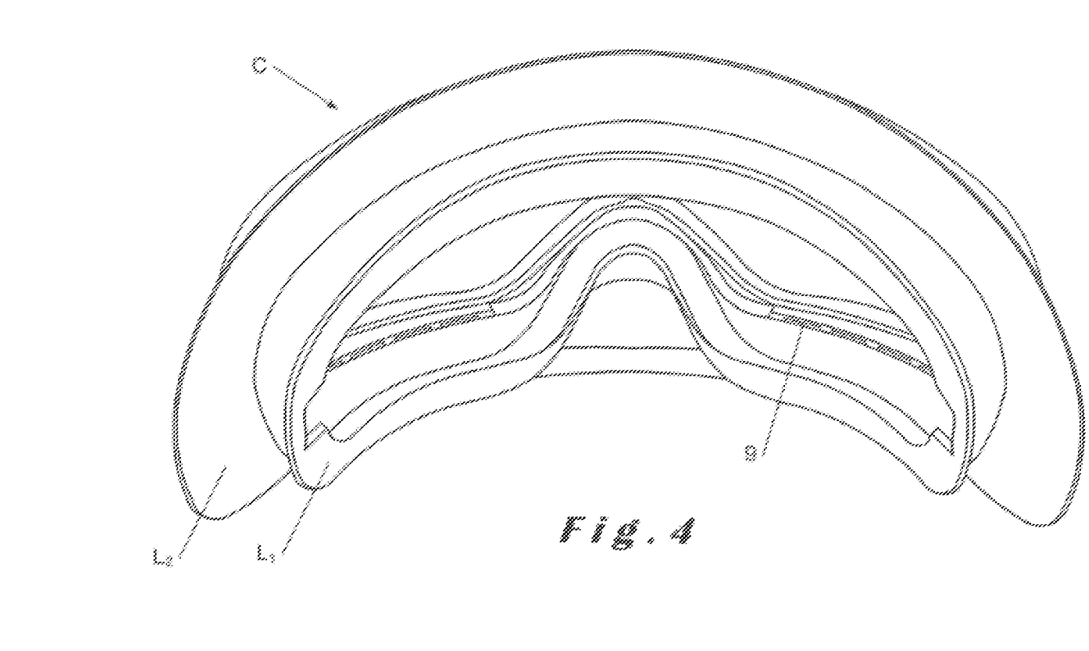
FIG. 4 is a perspective view showing a frame for a head protection hood according to the disclosure.

FIG. 4 shows a frame C for a head protection hood 1 according to the disclosure. In FIG. 4, the first lip L1, which is continuous and which is intended, when the hood 1 is worn by a user, to be in contact with and resting against the face of the user at an area between the bridge and tip of the nose, at the front region, at the temples and at the infra-orbital regions, thus forming a visual compartment 7, is visible. Air flow holes 9 situated along the lower wall of frame C are shown at the first frame section Pc1 extending towards the surrounding environment from the outer surface L2ext of the second peripheral lip L2. Preferably, the frame C also comprises other air flow holes (not visible) along its upper wall and on the first frame section Pc1 extending towards the surrounding environment from the outer surface L2ext of the second peripheral lip L2. Naturally, it is quite possible, according to the disclosure, that the frame C is not provided with any air flow hole or that these are only present in the upper wall or the lower wall of the frame C.

Due to the air flow holes 9 present in the frame C according to the disclosure, a flow of air is ensured in the visual compartment 7 in a way that further avoids any steam and condensation forming. This air flow is natural, as the hot air which is contained in the visual compartment 7 has a tendency to exit via the holes 9 present in the upper wall of the frame C, this leading to a natural aspiration of fresh air from the surrounding environment (for example, from the clean room) and via the holes 9 present in the lower wall of the frame C: the result is that the temperatures of the air in the visual compartment 7 and in the outer environment are practically identical, which contributes, however without being essential, to eliminating the presence of steam and condensation in the visor 6.

Figure 5A:
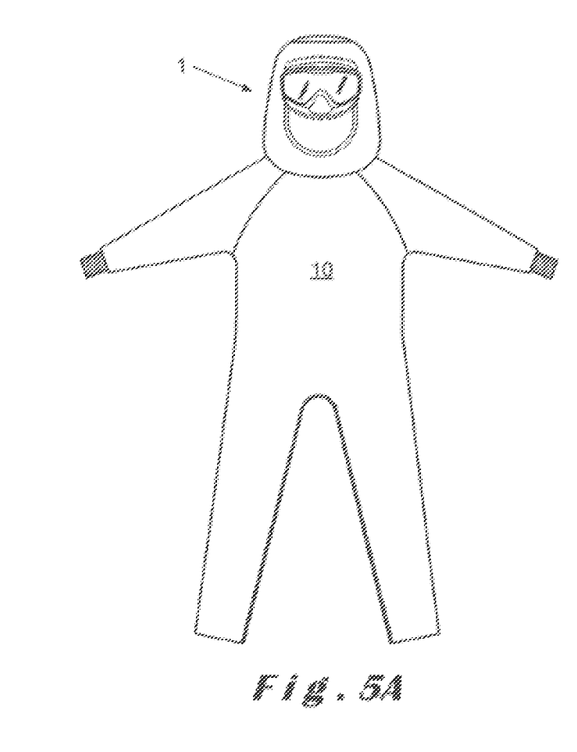
FIGS. 5A and 5B show a head protection hood according to the disclosure which is connected to and forms an integral part of a protective garment.
Figure 5B:
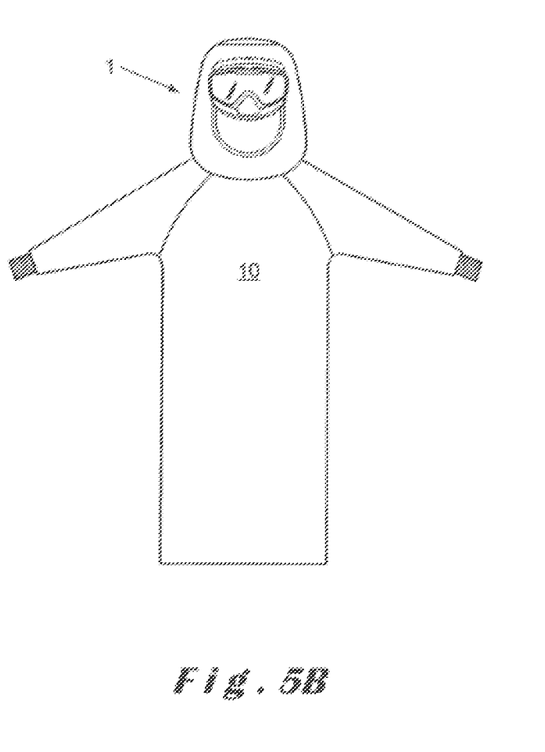

FIGS. 5A and 5B show a hood 1 according to the disclosure which connected to and forms an integral part of a protective garment 10, namely, for the example, overalls for clean rooms and similar. It is understood that the hood 1 may be connected by any appropriate means of fixing to the protective garment 10, for example by being sewn to it or by being fixed to it using a zip or snap fasteners. According to the disclosure, it is also intended that the head passage section 4 be at least partially covered by the protective garment 10 in such a way as to be at least partially inserted into the protective garment 10.

Figure 6:
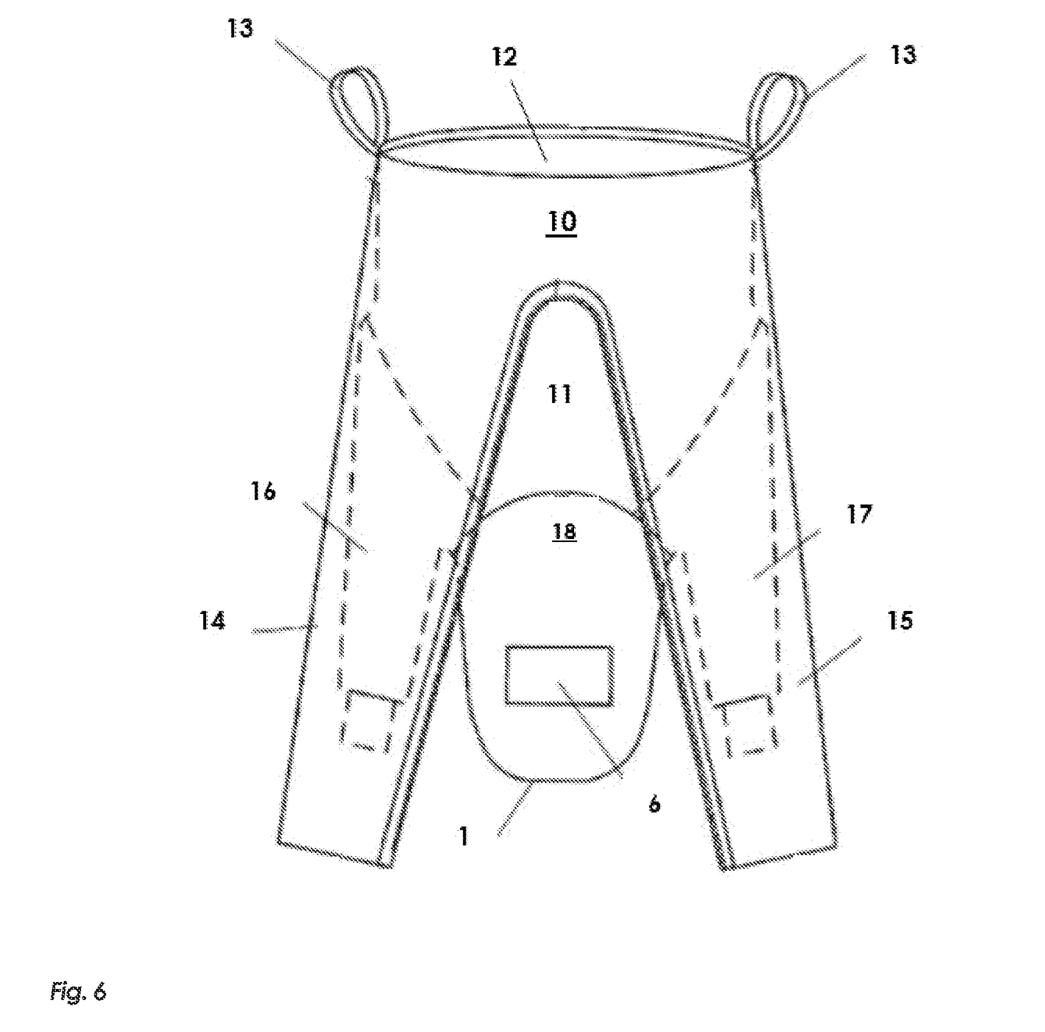
FIG. 6 shows a head protection hood according to an embodiment of disclosure, which is connected to and forms an integral part of a protective garment, such as the protective garment described in document EP2303044.

FIG. 6 shows a hood 1 according to embodiment of the disclosure in which it is connected to and forms an integral part of a protective garment 10, namely, for the example, overalls for clean rooms described in EP2303044. The overalls comprise an outer surface intended to be in contact with a surrounding environment and an inner surface intended to be in contact with a user. First and second leg sections (14, 15) are connected together by an opening in the crotch area (12). First and second sleeves (16,17) are connected by a connected end to torso section (11) and the first and second leg sections (14,15) are also connected to the torso section (11) by a connected end. The torso section (11) comprises a head passage section (18). The overalls further comprise at least one grip area (13) in contact with the inner surface in the torso section (11).

It is understood that the present disclosure is in no way limited to the embodiments described above and that changes may be applied while remaining within the scope of the attached claims.

The invention claimed is:

1. A head protection fabric hood, comprising:
    an outer surface configured to contact a surrounding environment;
    an inner surface configured to contact with a head of a user;
    a head passage section;
    a face opening delimited by an edge which is configured to be positioned at the eyes of the user;
    a breathing area; and
    a frame connected along the edge of the face opening, the frame receiving a visor, the frame having a first lip configured to rest on the head of the user at an area situated between the bridge and tip of the nose, at the front region, at the temples, and at the infra-orbital regions of the face of the user, thus forming a visual compartment separated from the breathing area,
    wherein the visor is a removable visor, the frame further comprises a second peripheral lip positioned between the first lip and the removable visor, the second peripheral lip extending from the frame in the direction of the surrounding environment and being connected to the fabric of the hood.

2. The head protection fabric hood according to claim 1, wherein the frame has a first frame section extending from an outer surface of the second peripheral lip towards the surrounding environment, and a second frame section configured to extend from an inner surface of the second peripheral lip towards the head of the user, the second frame section having the first lip.

3. The head protection fabric hood according to claim 2, wherein the first frame section has air flow holes.

4. The head protection fabric hood according to claim 1, wherein the first lip is continuous.

5. The head protection fabric hood according to claim 1, wherein the frame forms an integral part of the hood.

6. The head protection fabric hood according to claim 1, wherein the frame is formed of a material resistant to sterilization by gamma rays, beta rays, autoclaving, ethylene oxide treatments, or any combination thereof.

7. The head protection fabric hood according to claim 1, wherein the removable visor comprises a system for fixing to the frame.

8. The head protection fabric hood according to claim 1, wherein the removable visor is made of a transparent plastic material.

9. The head protection fabric hood according to claim 1, wherein the head protection fabric hood forms an integral part of a protective garment for clean room.

10. The head protection fabric hood according to claim 9, wherein the head protection fabric hood forms an integral part of a protective garment, comprising:
   an outer surface configured to contact the surrounding environment;
   an inner surface configured to contact the user;
   first and second leg sections connected together by an opening in the crotch area;
   first and second sleeves;
   a torso section to which the first and second sleeves and the first and second leg sections are connected, the torso section comprising an inner surface and a head passage section; and
   at least one grip area in contact with the inner surface of the torso section.

11. The head protection fabric hood according to claim 9, wherein the head protection fabric hood forms an integral part of a protective overalls having an opening in the torso section.

12. The head protection fabric hood according to claim 1, wherein the first lip is flexible.

13. The head protection fabric hood according to claim 1, wherein the removable visor is made of polycarbonate.

* * * * *